United States Patent
Yoon et al.

(10) Patent No.: US 10,688,143 B2
(45) Date of Patent: Jun. 23, 2020

(54) **COMPOSITION CONTAINING EXTRACT OR FRACTION OF GENUS *JUSTICIA* PLANT**

(71) Applicant: DONG WHA PHARM. CO., LTD., Seoul (KR)

(72) Inventors: Joo Byoung Yoon, Hwaseong-si (KR); Hyun Yong Lee, Yongin-si (KR); Ji Hyun Youm, Suwon-si (KR); Kwang Hyun Kim, Yongin-si (KR); Ji Hyun Jeon, Hwaseong-si (KR); Hwan Bong Chang, Yongin-si (KR); Yun Ha Hwang, Gunpo-si (KR); Seung Kyoo Seong, Incheon (KR); Dong Rack Choi, Seongnam-si (KR)

(73) Assignee: DONG WHA PHARM. CO., LTD., Seoul (KR)

( * ) Notice: Subject to any disclaimer, the term of this patent is extended or adjusted under 35 U.S.C. 154(b) by 413 days.

(21) Appl. No.: 15/519,116

(22) PCT Filed: Oct. 16, 2015

(86) PCT No.: PCT/KR2015/010994
§ 371 (c)(1),
(2) Date: Apr. 13, 2017

(87) PCT Pub. No.: WO2016/060525
PCT Pub. Date: Apr. 21, 2016

(65) Prior Publication Data
US 2017/0360862 A1 Dec. 21, 2017

(30) Foreign Application Priority Data
Oct. 16, 2014 (KR) ........................ 10-2014-0139734

(51) Int. Cl.
| | | |
|---|---|---|
| *A61K 36/19* | (2006.01) | |
| *A61P 11/02* | (2006.01) | |
| *A61P 17/00* | (2006.01) | |
| *A61P 27/16* | (2006.01) | |
| *A61P 37/08* | (2006.01) | |
| *A61P 27/14* | (2006.01) | |
| *A61K 8/9789* | (2017.01) | |
| *A61P 1/12* | (2006.01) | |
| *A61Q 19/00* | (2006.01) | |
| *A23L 33/105* | (2016.01) | |

(52) U.S. Cl.
CPC ............ *A61K 36/19* (2013.01); *A23L 33/105* (2016.08); *A61K 8/9789* (2017.08); *A61P 1/12* (2018.01); *A61P 11/02* (2018.01); *A61P 17/00* (2018.01); *A61P 27/14* (2018.01); *A61P 27/16* (2018.01); *A61P 37/08* (2018.01); *A61Q 19/00* (2013.01); *A23V 2002/00* (2013.01); *A61K 2236/33* (2013.01); *A61K 2236/331* (2013.01); *A61K 2236/35* (2013.01)

(58) Field of Classification Search
None
See application file for complete search history.

(56) References Cited

U.S. PATENT DOCUMENTS

| 6,365,411 B1 | 4/2002 | Subbiah et al. |
| 2015/0238404 A1 | 8/2015 | Ishikawa et al. |
| 2017/0360862 A1 | 12/2017 | Yoon et al. |

FOREIGN PATENT DOCUMENTS

| CN | 102327431 A | 1/2012 |
| DO | P2006000237 A | 8/2008 |
| EP | 2747573 A1 | 7/2014 |
| IN | 1330/MUM/2005 | 11/2005 |
| JP | 2007/230977 A | 9/2007 |
| JP | 2014/062090 A | 4/2014 |
| KR | 2016-0044807 A | 4/2016 |
| WO | 03055558 A1 | 7/2003 |
| WO | 2014/034802 A1 | 3/2014 |
| WO | 2017/179931 A1 | 10/2017 |

OTHER PUBLICATIONS

U.S. Appl. No. 16/093,829, filed Oct. 2018, Yoon; Joo Byoung.*
Pelaia, G., et. al., "Cellular Mechanisms Underlying Eosinophilic and Neutrophilic Airway Inflammation in Asthma", Mediators of inflammation, 2015 (9 pages).
Wilson, C. N., "Adenosine receptors and asthma in humans", British journal of pharmacology, 155(4), 475-486, 2008 (12 pages).
Dogra, K. S. et al., "Assessment of Indian Medicinal Plants for the Treatment of Asthma", Journal of Medicinal Plants Research, vol. 9, No. 32, 2015, pp. 851-862 (12 pages).
Zhou, P. et al., "Preparative Isolation and Purification of Lignans from Justicia Procumbens Using High-speed Countercurrent Chromatography in Stepwise Elution Mode", Molecules, vol. 20, 2015, pp. 7048-7058 (11 pages).
Savithramma, N. et al., "Ethnobotanical survey of plants used to treat asthma in Andhra Pradesh, India", Journal of Ethnopharmacology, vol. 113, pp. 54-61 (2007) (8 pages).
Rao, Y.K. et al., "Anti-inflammatory activities of constituents isolated from Phyllanthus polyphyllus" Journal of ethnopharmacology, 2006, 103(2), pp. 181-186 (6 pages).
Office Action issued in corresponding Indian Application No. 201717015734 dated Nov. 2, 2019 (6 pages).
TKDL Reference [GP04/76].
International Search Report and Written Opinion dated Jan. 28, 2016, issued by the Korean Intellectual Property Office (KIPO) in corresponding International Application No. PCT/KR2015/010994, with English translation (22 pages).

(Continued)

*Primary Examiner* — Michael Barker
(74) *Attorney, Agent, or Firm* — Osha Liang LLP

(57) ABSTRACT

The present invention relates to a pharmaceutical composition, food composition and cosmetic composition for preventing, treating, or improving allergic diseases comprising extract or fraction of a plant of the *Justicia* genus as an active ingredient. The extract or a fraction of a plant of the *Justicia* genus according to the present invention can inhibit IgE antibody secretion and the degranulation of mast cells and basophils, and exhibits an excellent anti-allergic effect, and thus can effectively prevent, treat, or improve allergic diseases.

8 Claims, 1 Drawing Sheet

(56) References Cited

OTHER PUBLICATIONS

PCT International Preliminary Report on Patentability (IPRP) dated Apr. 18, 2017, by the International Bureau of WIPO in corresponding International Application No. PCT/KR2015/010994, with English translation (17 pages).
Notification of Reason for Refusal (Office Action) dated Aug. 31, 2016, by the Korean Intellectual Property Office (KIPO) in corresponding Korean Patent Application No. KR 10-2014-0139734, with English translation (15 pages).
Hansbro, Philip M., et al., "Cytokine/anti-cytokine therapy—novel treatments for asthma?"; British Journal of Pharmacology (2011) vol. 163 (Themed Issue: Respiratory Pharmacology); pp. 81-95.
Asano, Jun, et al., "Antiviral Activity of Lignans and Their Glycosides From Justicia Procumbens"; Phytochemistry, vol. 42, No. 3, 1996; Elsevier Science Ltd.; Pergamon S031-9422(96)00024-6; pp. 713-717.
Fukamiya, Narihiko, et al., "Antitumor Agents, 81.1 Justicidin-A and Diphyllin, Two Cytotoxic Principles From Justicia Procumbens"; Journal of Natural Products, vol. 49, No. 2; Mar.-Apr. 1986; pp. 348-350.
Velpandian, V., et al., "Clinical Evaluation of *Justicia tranquebariensis* L. In the Management of Bronchial Asthma"; American Journal of Phytomedicine and Clinical Therapeutics, vol. 9, ISSN: 2321-2748; www.ajpct.org; Sep. 30, 2014; pp. 1103-1111.
Mitsuyasu, Hiromichi, et al., "Ile50Val variant of IL4Ra upregulates IgE synthesis and associates with atopic asthma"; Nature Genetics vol. 19, No. 2, Jun. 1998; 1998 Nature America Inc.—http://genetics.nature.com; pp. 119-120.
Shimoda, Kazuya, et al., "Lack of IL-4-induced Th2 response and IgE class switching in mice with disrupted Stat6 gene"; Nature, vol. 380, Apr. 18, 1996; pp. 630-633.
Bjorck, T., et al., "Leukotrienes and Histamine Mediate IgE-dependent Contractionis of Human Bronchi: Pharmacological Evidence Obtained with Tissues from Asthmatic and Non-asthmatic Subjects"; Pulmonary Pharmacology (1993) vol. 6, No. 1; pp. 87-96.
Stone, Kelly D., MD, PhD, et al., "IgE, mast cells, basophils, and eosinophils"; Journal of Allergy and Clinical Immunology, vol. 125, No. 2, Feb. 2010; Elsevier, Inc. on behalf of the American Academy of Allergy, Asthma & Immunology, doi: 10.1016/j.jaci.2009.11.017; pp. S73-S80.
Mullarkey, Michael F., M.D., et al., "Allergic and nonallergic rhinitis: Their characterization with attention to the meaning of nasal eosinophilia"; Journal of Allergy and Clinical Immunology, vol. 65, No. 2, 1980; pp. 122-126.
Humbles, Alison A., et al., "A Critical Role for Eosinopils in Allergic Airways Remodeling"; Science, vol. 305, Sep. 17, 2004; www.sciencemag.org.; pp. 1776-1779.
Grewe, Markus, et al., "A role for Th1 and Th2 cells in the immunopathogenesis of atopic dermatitis"; Immunology Today, vol. 19, No. 8, Elsevier Science Ltd., 0167-5699/98; PII: S0167-5699(98)01285.7; pp. 359-361.
Van Oosterhout, Antoon J. M., et al., "Effect of Anti-IL-5 and IL-5 on Airway Hyperreactivity and Eosinophils in Guinea Pigs"; American Review of Respiratory Disease, vol. 147, No. 3, 1993; pp. 548-552.
Ying, Sun, et al., "Eosinophil Chemotactic Chemokines (Eotaxin, Eotaxin-2, RANTES, Monocyte Chemoattractant Protein-3 (MCP-3), and MCP-4), and C—C Chemokine Receptor 3 Expression in Bronchial Biopsies from Atopic and Nonatopic (Intrinsic) Asthmatics1"; The Journal of Immunology, vol. 163, No. 11, 1999; pp. 6321-6329.
Salpeter, Shelley R., MD, et al., "Meta-Analysis: Effect of Long-Acting β-Agonists on Severe Asthma Exacerbations and Asthma-Related Deaths"; Annals of Internal Medicine, vol. 144, No. 12, Jun. 20, 2006; downloaded from: http://annals.org/ on Nov. 1, 2016; pp. 904-912.
De Haan, Jacco J., et al., "Lipid-rich enteral nutrition regulates mucosal mast cell activation via the vagal anti-inflammatory reflex"; American Journal of Physiology-Gastrointestinal and Liver Physiology, vol. 305, No. 5; Jun. 27, 2013; doi: 10.1152/ajpgi.00333.2012; http://www.ajpgi.org; 0193-1857/13 2013 The American Physiological Society; pp. G383-G391.
Sewell, William A., et al., "Induction of Interleukin-4 and Interleukin-5 Expression in Mast Cells is Inhibited by Glucocorticoids"; Clinical and Diagnostic Laboratory Immunology, vol. 5, No. 1, Jan. 1998; American Society for Microbiology, 1998, 1071-412X/98; pp. 18-23.
Office Action issued in corresponding Russian Application No. 2017116794/15(029034) dated Oct. 5, 2018, and English translation thereof (20 pages).
Chaukhamba Orientalia, Varanasi, and.8th, 1998 [time of origin 5th century], Indian database TKDL, document RS23/1486: http://www.tkdl.res.in/tkdl/LangDefault/Formulation/Member_Docs/BC/ <https://protect-us.mimecast.com/s/Jrk5Czp9YZuE31Xf4t2Mq?domain=tkdl.res.in> ayurveda/highlight.asp?a=/tkdl/LangDefault/Formulation/Member_Docs/ BC/Ayurveda/RS23-1486.asp&b=justicia+and+allergic?str=Global (2 pages).
Chaukhamba Sanskrit Sansthan, Varanasi, and.14th, 2001 [this book contains back references from 1000 B.C. to 18th century], Indian database TKDL, document AK/3011: http://www.tkdl.res.in/tkdl/LangDefault/Formulation/Member_Docs/BC/ <https://protect-us.mimecast.com/s/Jrk5Czp9YZuE31Xf4t2Mq?domain=tkdl.res.in> ayurveda/highlight.asp?a=/tkdl/LangDefault/Formulation/Member_Docs/ BC/Ayurveda/AK3011.asp&b=justicia+and+allergic?str=Global (5 pages).
Office Action issued in corresponding Japanese Application No. 2017-540535 dated Jan. 23, 2018, and English translation thereof (12 pages).
Office Action issued in corresponding Australian Application No. 2015331082 dated Apr. 3, 2018 (5 pages).
Extended European Search Report issued in corresponding European Application No. 15851222.8 dated Apr. 18, 2018 (13 pages).
Geone M. Correa et al: "Chemical constituents and biological activities of species of *Justicia*—a review", Revista Brasileira de Farmacognosia Brazilian Journal of Pharmacognosy, Nov. 1, 2011, pp. 220-238 (19 pages).
Youm Jihyun et al: "DW2008S and its major constituents from Justicia procumbens exerts anti-asthmatic effect via multitargeting activity.", Journal of Cellular and Molecular Medicine, Mar. 7, 2018 (12 pages).
Youm Jihyun et al: "Justicia procumbens Extract (DW2008) Selectively Suppresses Th2 Cytokenis in Splenocytes and Ameliorates Ovalbumin-Induced Airway Inflammation in a mouse model of asthma", Biological and Pharmaceutical Bulletin, vol. 40, No. 9, Sep. 2017, pp. 1416-1422 (7 pages).
Adams, M. and Bauer, R., "Inhibition of Leukotriene Biosynthesis by Secondary Plant Metabolites", (2008) Current Organic Chemistry vol. 12 Issue 8, pp. 602-618 (17 pages).
Therien, M. et al. "Justicidin E: A New Leukotriene Biosynthesis Inhibitor" (1993) Bioorganic & Medicinal Chemistry Letters, vol. 3 No. 10, pp. 2063-2066 (4 pages).
Natural medicinal herbs medicinal herbs Justicia procumbens, Internet, viewed on Apr. 3, 2018 (http://www.naturalmedicinalherbs.net/herbs/j/justicia-procumbens.php) (1 page).
Meneki Seibutsugaku(Immunobiology (Seventh Edition)), 2010, pp. 566-569 (5 pages).

* cited by examiner

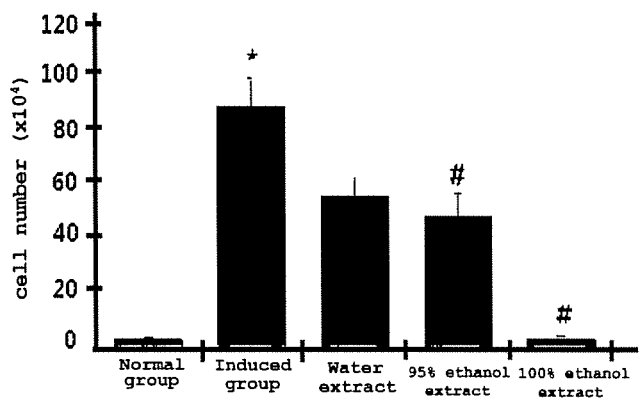
(n=5, *p<0.05 vs. normal group, #p<0.05 vs. induced group)
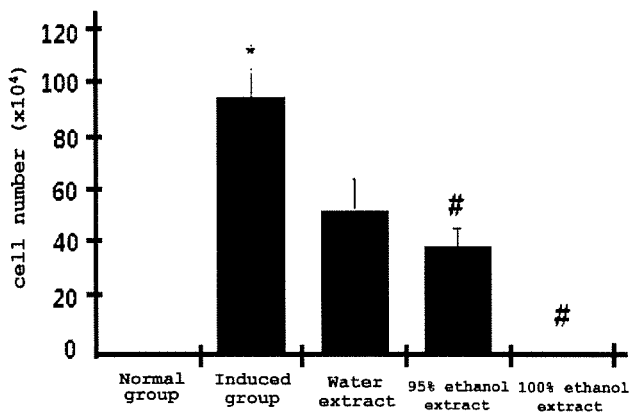
(n=5, *p<0.05 vs. normal group, #p<0.05 vs. induced group)

COMPOSITION CONTAINING EXTRACT OR FRACTION OF GENUS *JUSTICIA* PLANT

CROSS REFERENCE TO RELATED APPLICATIONS

This is a national stage application of PCT/KR2015/010994, filed on Oct. 16, 2015, which claims the priority of Korean Patent Application No. 10-2014-0139734, filed on Oct. 16, 2014. This application claims the benefit and priority of these prior applications and incorporates their disclosures by reference in their entirety.

TECHNICAL FIELD

The present invention relates to a pharmaceutical composition, food composition and cosmetic composition for the preventing, treating or improving of allergic disease an extract of a plant of the *Justicia* genus or a fraction thereof as an active ingredient.

BACKGROUND ART

The *Justicia* genus of the family Acanthaceae is the largest genus in the family Acanthaceae, consists of about 600 species, and is found in pantropical and tropical climate areas. Plants belonging to the *Justicia* genus are perennial plants or subshrubs and are easily recognized by their lip-shaped corolla. Typical plants belonging to the *Justicia* genus include *Justicia procumbens* L., *Justicia pectoralis* Jacq., *Justicia gendarussa* Burm. f., *Justicia anselliana*, and *Justicia adhatoda* L, etc., but the physiological activities of plants of the *Justicia* genus have not yet been sufficiently studied.

*Justicia procumbens* L. belonging to the *Justicia* genus of the Acanthaceae is an annual plant and is distributed in Korea, Japan, China, India, etc. *Justicia procumbens* L. has a height of about 30 cm, and its leaves are opposite leaves, long oval in shape, 2-4 cm in length, and 1-2 cm in width. In addition, both ends of the leaf are pointed, and the edges of the leaf are elliptical or have a wave shape. The flower of the plant is light magenta in color, blooms in July to September, and bear fruit in September to October.

In 1963, Gell P. G. H. & Coombs R. R. A largely classified hypersensitivity, which occurs in the human body, into four types: type I hypersensitivity corresponding acute allergic reactions, and type II-IV hypersensitivity corresponding to non-allergic reactions such as autoimmune diseases (Gell P G H & Coombs R R A, et al. Oxford, England: Blackwell, 1963).

Allergy is defined as a phenomenon in which a living body coming in contact with a foreign substance called allergen shows abnormal responses to the substance. Allergy can be caused not only by various allergens, including pollen, drugs, vegetable fibers, bacteria, foods, hair dyes, chemicals, etc., but also by humidity, temperature, exercise, etc, and can cause various diseases such as allergic rhinitis, asthma, atopic dermatitis, allergic conjunctivitis, allergic otitis media, allergic gastroenteritis, anaphylaxis and urticaria.

Allergic reactions are characterized by being dependent mostly on IgE antibody, and allergic reactions that are mediated by this IgE antibody are named "atopy" (Mitsuyasu et al. Ile50Val variant of IL4Rα upregulates IgE synthesis and associates with atopic asthma. *Nature genetics* 19.2, 119-120, 1998). Th2 lymphocytes activated by allergen secrete various physiologically active substances (cytokines) such as interleukin-4 (IL-4) or interleukin-5 (IL-5), and these physiologically active substances stimulate B lymphocytes to promote IgE antibody secretion (SHIMODA et al. Lack of IL-4-induced Th2 response and IgE class switching in mice with disrupted State6 gene. *Nature* 380, 630-633, 1996). The secreted IgE antibodies bind to FceR1 on the surface of cells such as mast cells or basophils to activate these cells. It is known that the activated cells are degranulated to promote the secretion of various physiologically active substances including histamine, leukotrien, prostaglandin D2 or the like that cause various allergic disease-related reactions such as vasodilation, smooth muscle contraction, mucous secretion or the like, and various respiratory disease-related reactions such as airway inflammation, airway contraction or the like (Bjorck, T., & Dahlen, S. E. Leukotrienes and histamine mediate IgE-dependent contractions of human bronchi: pharmacological evidence obtained with tissues from asthmatic and non-asthmatic subjects. *Pulmonary pharmacology,* 6(1), 87-96, 1993; Stone et al., IgE, mast cells, basophils, and eosinophils. *Journal of Allergy and Clinical Immunology,* 125(2), S73-S80, 2010).

Furthermore, it was reported that allergic reactions can cause eosinophilia in which the number of eosinophils in blood increases and which is associated with allergic rhinitis and asthma, atopic dermatitis, etc. (Mullarkey et al. Allergic and nonallergic rhinitis: their characterization with attention to the meaning of nasal eosinophilia. *Journal of Allergy and Clinical Immunology* 65.2 122-126, 1980; Humbles et al. Acritical role for eosinophils in allergic airways remodeling. *Science* 305.5691, 1776-1779, 2004; Grewe et al. A role for Th1 and Th2 cells in the immunopathogenesis of atopic dermatitis. *Immunology today* 19.8, 359-361, 1998). Particularly, it is known that an increase in the number of eosinophils in lung tissue is a major factor that causes eosinophilic asthma and eosinophilic pneumonia and that interleukin-5 and eotaxin are substances that induce an increase in the number of eosinophils in a particular tissue (Van Oosterhout et al. Effect of anti-IL-5 and IL-5 on airway hyperreactivity and eosinophils in guinea pigs *American Review of Respiratory Disease* 147.3, 548-552, 1993; Ying et al. Eosinophil chemotactic chemokines (eotaxin, eotaxin-2, RANTES, monocyte chemoattractant protein-3 (MCP-3), and MCP-4), and CC chemokine receptor 3 expression in bronchial biopsies from atopic and nonatopic (Intrinsic) asthmatics. *The Journal of Immunology* 163.11, 6321-6329, 1999).

Based on the studies as described above, there have been steady efforts to inhibit IgE antibody secretion, inhibit the degranulation of mast cells or basophils, and block the entry of inflammatory cells such as eosinophils, thereby preventing, treating or improving allergic disease.

Allergy-related diseases are classified, according to the body area in which symptoms occurred, into allergic rhinitis, asthma, hypersensitive pneumonitis, eosinophilic pneumonia, atopic dermatitis, contact dermatitis, urticaria, angioedema, anaphylaxis, allergic conjunctivitis, eosinophilic gastroenteritis, oral allergy syndrome, etc. In addition, allergy-related diseases are classified, according to the cause, into occupational asthma, occupational rhinitis, occupational dermatitis, food-induced urticaria, food-dependent anaphylaxis, anaphylaxis occurring after insect bites, skin rash caused by the wearing of rubber gloves, drug-induced urticaria, anaphylaxis occurring after examination with contrast medium vessel, Churg-Strauss syndrome, idiopathic eosinophilia, etc.

As therapeutic agents for treating allergic diseases, antihistamine drugs, antileukotriene drugs, steroidal drugs and the like have been mainly used, but the use thereof is limited because of their effects and side effects.

Specifically, antihistamine drugs, decongestants, antileukotriene drugs and the like have been used to treat allergic rhinitis. However, antihistamine drugs can cause side effects such as sleepiness, and decongestants such as pseudoephedrine are narcotic components that can cause headache or stroke, and antileukotriene drugs can cause neuropsychiatry-related side effects such as depression, suicide impulse or the like.

More specifically, drugs that are used to treat asthma include antileukotriene drugs, steroidal drugs, beta-2 adrenergic agonists, anti-IgE drugs (Omalizumab) and the like. Herein, in the case of antileukotriene drugs, it is mainly used as mild or add-on therapy, because these cause side effects as described above and also have insignificant effects on asthma. Steroidal therapeutic agents are used mainly for inhalation rather than oral administration due to their side effects, and thus shows poor compliance compared to oral drugs. In addition, beta-2 adrenergic agonists are also inhalation drugs that alleviate asthma symptoms by effectively inhibiting bronchoconstriction through local smooth muscle relaxation of the lung, but do not radically cure asthma and may exacerbate asthma upon long-term administration (Salpeter, et al. Meta-analysis: effect of long-acting β-agonists on severe asthma exacerbations and asthma-related deaths. *Annals of internal medicine* 144.12 904-912, 2006). Anti-IgE drugs (Omalizumab) are used for severe asthma resistant to steroids/beta-2 adrenergic agonists and have excellent effects, but have disadvantages in that they are expensive and are used as injectable formulations that are not easy to administer.

For treatment of atopic dermatitis, steroidal drugs, immunosuppressants/immunomodulators, antihistamine drugs etc., are used. Immunosuppressants such as Tacrolimus have excellent effects, but can cause side effects such as hypertension, reduced renal function or the like.

As described above, it is obvious that agents that are currently used to treat allergy-related diseases are limited in their use, and thus there is an urgent need to develop new therapeutic agents. In addition, because of complex action mechanisms associated with allergy, there is increasing interest in herbal extracts having effects on a combination of various mechanisms through various components, rather than single-component synthetic drugs that mainly control single targets. However, reports on herbal extracts having excellent effects against a combination of various allergic diseases are still insufficient. Accordingly, there is an urgent need to develop new herbal plant extracts that are safe for use in vivo and that can substitute for conventional anti-allergic drugs.

DISCLOSURE

Technical Problem

The present inventors have conducted studies on a plant of the *Justicia* genus, and as a result, have found that an extract of a plant of the *Justicia* genus or a fraction thereof effectively inhibits IgE antibody secretion and inhibits degranulation of mast cells and basophils, and shows excellent anti-allergic effects in various allergic disease animal models, thereby completing the present invention.

Therefore, it is an object of the present invention to provide a pharmaceutical composition for preventing or treating allergic disease comprising an extract of a plant of the *Justicia* genus or a fraction thereof.

Another object of the present invention is to provide an anti-allergic agent comprising an extract of a plant of the *Justicia* genus or a fraction thereof as an active ingredient.

Still another object of the present invention is to provide a food composition for preventing or improving allergic disease comprising an extract of a plant of the *Justicia* genus or a fraction thereof as an active ingredient.

Still another object of the present invention is to provide a cosmetic composition for preventing or improving allergic disease comprising an extract of a plant of the *Justicia* genus or a fraction thereof as an active ingredient.

Still another object of the present invention is to provide the use of an extract of a plant of the *Justicia* genus or a fraction thereof for the prevention or treatment of allergic disease.

Still another object of the present invention is to provide a method for preventing or treating allergic disease comprising a step of administering to a subject a composition comprising an extract of a plant of the *Justicia* genus or a fraction thereof.

Yet another object of the present invention is to provide the use of an extract of a plant of the *Justicia* genus or a fraction thereof for manufacture of a medicament for preventing or treating allergic disease.

Technical Solution

To achieve the above objects, the present invention provides a pharmaceutical composition for preventing or treating allergic disease comprising an extract of a plant of the *Justicia* genus or a fraction thereof as an active ingredient.

The present invention also provides a pharmaceutical composition for preventing or treating allergic disease, wherein a plant of the *Justicia* genus is one or more selected from the group consisting of *J. adhatoda* L., *J. albobracteata* L, *J. anselliana*, *J. aurea* Schltdl., *J. betonica*, *J. calycina*, *J. ciliate*, *J. comata* L., *J. diffusa*, *J. dumetorum*, *J. extensa*, *J. flava*, *J. gendarussa* Burm. f., *J. ghiesbreghtiana*, *J. glauca*, *J. hayatai*, *J. heterocarpa* T. Anders., *J. hyssopifolia* L., *J. ideogenes*, *J. insularis*, *J. neesii*, *J. pectoralis* Jacq., *J. plectrantus*, *J. prostrate*, *J. purpurea*, *J. reptans*, *J. rhodoptera*, *J. schimperiana*, *J. secunda*, *J. sericea*, *J. simplex*, *J. spicigera*, *J. valida*, and *J. procumbens* L.

The present invention also provides a pharmaceutical composition for preventing or treating allergic disease, wherein a plant of the *Justicia* genus is *Justicia procumbens* L.

The present invention also provides a pharmaceutical composition for preventing or treating allergic disease, wherein the *Justicia procumbens* L. is one or more selected from the group consisting of the whole plant, aerial part, root, leaf and flower of the *Justicia procumbens* L.

The present invention also provides a pharmaceutical composition for preventing or treating allergic disease, wherein the extract is an organic solvent extract.

The present invention also provides a pharmaceutical composition for preventing or treating allergic disease, wherein the organic solvent is one or more selected from the group consisting of a lower alcohol having 1 to 4 carbon atoms, hexane, ethyl acetate, dichloromethane, ether, chloroform, and acetone.

The present invention also provides a pharmaceutical composition for preventing or treating allergic disease, wherein the lower alcohol having 1 to 4 carbon atoms is one or more selected from the group consisting of methanol, ethanol, propanol, isopropanol, butanol and n-butanol.

The present invention also provides a pharmaceutical composition for preventing or treating allergic disease, wherein the fraction is an organic solvent fraction obtained by fractionation with an organic solvent selected from the group consisting of n-hexane, ethyl acetate and water-saturated n-butanol.

The present invention also provides a pharmaceutical composition for preventing or treating allergic disease, wherein the fraction is a water fraction excluding an organic solvent.

The present invention also provides a pharmaceutical composition for preventing or treating allergic disease, wherein the allergic disease is allergic respiratory disease.

The present invention also provides a pharmaceutical composition for preventing or treating allergic disease, wherein the allergic disease is one or more selected from the group consisting of rhinitis, asthma, atopic dermatitis, allergic conjunctivitis, allergic otitis media, allergic gastroenteritis, anaphylaxis and urticaria.

The present invention also provides an anti-allergic agent comprising an extract of a plant of the *Justicia* genus or a fraction thereof as an active ingredient.

The present invention also provides a food composition for preventing or improving allergic disease comprising an extract of a plant of the *Justicia* genus or a fraction thereof as an active ingredient.

The present invention also provides a food composition wherein the food is a functional health food.

The present invention also provides a cosmetic composition for preventing or improving allergic disease comprising an extract of a plant of the *Justicia* genus or a fraction thereof as an active ingredient.

The present invention also provides the use of an extract of a plant of the *Justicia* genus or a fraction thereof for the prevention or treatment of allergic disease.

The present invention also provides a method for preventing or treating allergic disease, the method comprising a step of administering to a subject a composition comprising an extract of a plant of the *Justicia* genus or a fraction thereof.

The present invention also provides the use of an extract of a plant of the *Justicia* genus or a fraction thereof for manufacture of a medicament for preventing or treating allergic disease.

Advantageous Effects

An extract of a plant of the *Justicia* genus or a fraction thereof according to the present invention can effectively prevent, treat or improve allergic disease.

DESCRIPTION OF DRAWINGS

FIG. 1 shows the results of confirming the reduction in number of inflammatory cells in bronchoalveolar lavage fluids, caused by *Justicia procumbens* extracts according to the present invention.

BEST MODE

The present invention provides a pharmaceutical composition for preventing or treating allergic disease comprising an extract of a plant of the *Justicia* genus or a fraction thereof as an active ingredient.

In the present invention, "the *Justicia* genus of the family Acanthaceae" is the largest genus in the family Acanthaceae, consists of about 600 species, and is a plant found in pantropical and tropical climate areas.

In the present invention, "a plant of the *Justicia* genus" refers to a plant belonging to the *Justicia* genus of the family Acanthaceae. In the present invention, any plant belonging to the *Justicia* genus of the family Acanthaceae may be used without limitation, as long as an extract thereof or a fraction of the extract can exhibit anti-allergic effects so that it can be used against allergic disease. This plant of the *Justicia* genus may preferably be one or more selected from the group consisting of *J. adhatoda* L., *J. albobracteata* L, *J. anselliana*, *J. aurea* Schltdl., *J. betonica*, *J. calycina*, *J. ciliate*, *J. comata* L., *J. diffusa*, *J. dumetorum*, *J. extensa*, *J. flava*, *J. gendarussa* Burm. f., *J. ghiesbreghtiana*, *J. glauca*, *J. hayatai*, *J. heterocarpa* T. Anders., *J. hyssopifolia* L., *J. ideogenes*, *J. insularis*, *J. neesii*, *J. pectoralis* Jacq., *J. plectrantus*, *J. prostrate*, *J. purpurea*, *J. reptans*, *J. rhodoptera*, *J. schimperiana*, *J. secunda*, *J. sericea*, *J. simplex*, *J. spicigera*, *J. valida*, and *J. procumbens* L.

Among these plants, "*Justicia procumbens* L. of the *Justicia* genus of the family Acanthaceae" is an annual plant and is distributed in Korea, Japan, China, India, etc. It has a height of about 30 cm, and its leaves are opposite leaves, long oval in shape, 2-4 cm in length, and 1-2 cm in width. In addition, both ends of the leaf are pointed, and the edges of the leaf are elliptical or have a wave shape. The flower of a plant is light magenta in color, blooms in July to September, and bears fruit in September to October. The whole plant of *Justicia procumbens* L. is harvested in the fall season and is used after drying. It was reported that the whole plant of *Justicia procumbens* L. has effects on heat clearance, detoxification, dampness removal, blood circulation activation, and pain alleviation, and can be used against bacterial diarrhea, jaundice, nephritis edema, muscle and bone pain, contusions, etc.

An extract of a plant of the *Justicia* genus or a fraction thereof according to the present invention can inhibit IgE antibody secretion and the degranulation of mast cells and basophils. Particularly, it is useful for inhibition of Th2 immune function and exhibits excellent anti-allergic effects. Thus, it can prevent, treat or improve allergic disease.

If the extract of a plant of the *Justicia* genus or a fraction thereof according to the present invention is a mixed extract or a mixed fraction, which comprises, as an active ingredient, an extract of two or more plants of the genus *Justicia* or a fraction of the extract, it may be either a mixed extract obtained by extracting a mixture of a plants or a fraction of the mixed extract, or a mixed extract obtained by extracting each of a plant and mixing the extracts, or a fraction of the mixed extract, but is not limited thereto.

In the present invention, a more preferred plant of the *Justicia* genus is, for example, *Justicia procumbens* L.

A plant of the *Justicia* genus, which is used in the present invention, may be used commercially purchased or be a cultivated plant without limitation, and the whole plant, aerial part, leaf, root, stem, flower or the like of a plant may be included without limitation. Most preferably, the whole plant or aerial part of a plant may be used.

The extract of a plant of the *Justicia* genus according to the present invention may be a water or organic solvent extract. Preferably, it may be an organic solvent extract, an organic solvent crude extract, or a concentrate thereof. The organic solvent is preferably one or more selected from the group consisting of a lower alcohol having 1 to 4 carbon atoms, hexane, ethyl acetate, dichloromethane, ether, chloroform, and acetone. The lower alcohol having 1 to 4 carbon atoms is preferably one or more selected from the group consisting of methanol, ethanol, propanol, isopropanol, butanol and n-butanol, and the lower alcohol having 1 to 4 carbon atoms may comprise an anhydrous or hydrated alcohol having 1 to 4 carbon atoms. The alcohol, for example, ethanol or isopropanol, may be 1 to 100% (v/v), preferably 30 to 100% (v/v), more preferably 70 to 100% (v/v), even more preferably 90% (v/v), 95% (v/v), or 100% (v/v) alcohol. When butanol is used as an extraction solvent, it is preferably water-saturated butanol (an aqueous solution of 75-85% (v/v) butanol).

The present invention also provides a pharmaceutical composition for preventing or treating allergic disease comprising an extract of a plant of the *Justicia* genus or a fraction thereof as an active ingredient, wherein the "fraction" may be a fraction (secondary extract) obtained by concentrating a crude extract of *Justicia procumbens* L. and fractionating the concentrate by adding lower alcohols having 1 to 4 carbon atoms, aqueous solutions thereof or non-polar solvents individually (or in combination).

The lower alcohols having 1 to 4 carbon atoms may preferably be selected from the group consisting of ethanol, methanol, propanol, isopropanol, butanol and n-butanol. The non-polar solvents may be selected from the group consisting of hexane, ethyl acetate, ether, dichloromethane, chloroform and butanol, and may preferably be n-hexane, ethyl acetate and water-saturated n-butanol. In addition, the fraction may be a water fraction excluding each organic solvent layer.

The extract or fraction of the present invention may include not only an extract or fraction obtained using the above-described extraction solvent, but also an extract or fraction subjected to a conventional purification process. For example, fractions obtained through various additional purification methods, such as separation with an ultra filtration membrane having a given molecular weight cut-off, separation by various chromatography systems (manufactured for separation according to size, charge, hydrophobicity or affinity), are also included in the scope of the fraction of the present invention.

The extract or fraction of the present invention may be prepared into powder by additional processes such as vacuum distillation and freeze-drying or spray-drying.

The extract of a plant of the *Justicia* genus or a fraction thereof according to the present invention may be prepared by a process comprising the following steps, but is not limited thereto:

1) a step of crushing and air curing a plant of the *Justicia* genus;
2) a step of extracting the crushed plant of the *Justicia* genus to obtain an extract; and
3) a step of filtering the extract, followed by concentration under reduced pressure.

The plant of the *Justicia* genus used in step 1) may be a cultivated plant or a commercially available plant.

The extraction in step 2) may be dipping (cold or hot extraction), hot-water extraction, ultrasonic extraction or reflux cooling extraction. Preferably, it is reflux extraction. The extraction may be performed at a temperature of 40 to 120° C., preferably 80 to 100° C. The extraction may be performed for 1 to 24 hours, preferably 1 to 10 hours, and more preferably 1 to 5 hours. In addition, the extraction of the present invention may be performed 1 to 5 times, preferably 2 or 3 times, depending on extraction efficiency, but is not limited thereto.

In order to obtain the fraction of the extract of the plant of the *Justicia* genus, 5-20-fold (v/w) purified water may be added to the concentrate of the primary extract to suspend the concentrate therein, and then organic solvents selected from the group consisting of hexane, ethyl acetate, butanol (including water-saturated butanol), dichloromethane and chloroform may be individually (or sequentially) added to the suspension to perform extraction, thereby obtaining a fraction (secondary extract). Herein, the extraction temperature is 40 to 120° C., preferably 60 to 90° C., and the extraction time is 2 to 24 hours, preferably 4 to 12 hours. In addition, the extraction of the present invention may be performed 1 to 5 times, preferably 2 or 3 times, depending on extraction efficiency, but is not limited thereto.

The extract or fraction obtained as described above may be prepared into powder by removing the remaining lower alcohol and organic solvent by use of a conventional drying method such as drying under reduced pressure, spray-drying or freeze-drying so as to be suitable for use as a raw material for a medical drug.

Meanwhile, the allergic diseases in the present invention may include various diseases caused by various allergens without limitation, and include not only pathological symptoms attributable to antigen-antibody reactions, but also those that are very similar to diseases showing antigen-antibody reactions but do not show antigen-antibody reactions, or those that are highly likely to cause such reactions, etc. The allergic disease includes any disease appearing in the respiratory system, the digestive system, the circulatory system or the like. Preferably, the allergic disease is one or more selected from the group consisting rhinitis, asthma, atopic dermatitis, allergic conjunctivitis, allergic otitis media, allergic gastroenteritis, anaphylaxis and urticaria, or may be allergic respiratory disease.

For treatment of allergic disease, an extract of a plant of the *Justicia* genus or a fraction thereof may be used alone or in combination with one or more drugs or herbal extracts known to be effective against allergic disease. Particularly, where the extract or fraction of the present invention is to be used in a mixture with an extract of another plant, a plant may be extracted after mixing with a plant of the *Justicia* genus, or may be extracted separately and mixing with the extract of a plant of the *Justicia* genus or the fraction thereof.

Examples of an extract or a fraction thereof, which is effective against allergic disease and may be used in combination with an extract of a plant of the *Justicia* genus or a fraction thereof, include a mixture of the extract of a plant of the *Justicia* genus or the fraction thereof with an *Andrographis paniculata* extract or a fraction thereof, a mixture of the extract of a plant of the *Justicia* genus or the fraction thereof with a *Sida rhombifolia* extract or a fraction thereof, a mixture of the extract of a plant of the *Justicia* genus or the fraction thereof with a *Chamaecrista nomame* extract or a fraction thereof, a mixture of the extract of a plant of the *Justicia* genus or the fraction thereof with a *Lagerstroemia indica* L. extract or a fraction thereof, etc. In addition, the extract of a plant of the *Justicia* genus or the fraction thereof may be used in combination with extracts or fractions thereof from various plants, including *Salvia plebeian, Mimosa pudica, Eclipta prostrate, Tussilago farara, Fraxini* cortex, *Vitis vinifera* leaf, *Raphani* semen, *Tribulus terrestris* L., *Euryale* seed, *Rhenm undulatum* L., *Lindera strychnifolium, Fallopia japonica, Schijandra chinensis*, etc., which are expected to show anti-allergic reactions.

The composition according to the present invention may be formulated as a pharmaceutical formulation using a method well known in the art so as to provide quick, sustained or delayed release of the active ingredient after its administration to mammals. In preparation of a formulation, the composition according to the present invention is preferably mixed or diluted with a carrier or encapsulated in a capsule-shaped carrier.

Specifically, the pharmaceutical composition of the present invention may be formulated in the form of tablet, pill, powder, granule, capsule, suspension, solution, emulsion, syrup, aerosol, injectable solution or the like according to a conventional method well known in the art. Examples of carriers, excipients and diluents which may be contained in the pharmaceutical composition of the present invention include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxylbenzoate, talc, magnesium stearate, and mineral oil, etc. The composition of the present invention may be formulated with conventional diluents or excipients, such as fillers, extenders, binders, wetting agents, disintegrants, surfactants, etc, which are generally used.

Solid formulations for oral administration include tablets, pills, powders, granules, capsules and the like, and such solid formulations may comprise at least one excipient, for example, starch, calcium carbonate, sucrose, lactose, gelatin or the like. In addition to simple excipients, lubricants such as magnesium stearate or talc may also be used. Liquid formulations for oral administration include suspensions, solutions, emulsions, and syrup, and may contain various excipients, for example, wetting agents, flavoring agents, aromatics and preservatives, in addition to water and liquid paraffin, which are frequently used simple diluents.

Formulations for parenteral administration include sterilized aqueous solutions, non-aqueous solutions, suspensions, emulsions, freeze-dried preparations, suppositories, etc. As non-aqueous solvents or suspending agents, propylene glycol, polyethylene glycol, plant oils such as olive oil, injectable esters such as ethyl oleate, and the like can be used.

The pharmaceutical composition of the present invention may be administered in a pharmaceutically effective amount. As used herein, the term "pharmaceutically effective amount" refers to an amount sufficient to treat diseases, at a reasonable benefit/risk ratio applicable to any medical treatment. The effective dosage level of the composition may be determined by a person skilled in the art depending on various factors, including a formulation method, the patient's condition, body weight, sex and age, the severity of the disease, the form of drug, the route and duration of administration, excretion rate, and reaction sensitivity. As recognized by those skilled in the art, the effective amount may vary depending on the route of treatment, the use of excipients and the possibility of use with other drugs.

The dose or dosage of the extract of a plant of the *Justicia* genus or the fraction thereof according to the present invention may vary depending on the patient's body weight, age, sex, health condition, diet, the time of administration, the mode of administration, excretion rate, and the severity of the disease. However, the extract or fraction of the present invention is administered at a dose of 0.001 mg/kg to 1000 mg/kg once or several times a day for adults.

The pharmaceutical composition of the present invention may be administered via various routes to mammals, including mice, livestock and humans. For example, it may be administered orally, parenterally, intravenously, intradermally or by subcutaneous injection.

Therefore, the present invention provides a method for preventing or treating allergic disease a step of administering to a subject a composition comprising an extract of a plant of the *Justicia* genus or a fraction thereof.

The administration may be performed orally, parenterally, intravenously, intradermally or by subcutaneous injection. When the extract or the fraction thereof is to be administered to a subject, it may be administered in an effective amount required for the prevention or treatment of allergic disease. When the extract of a plant of the *Justicia* genus or the fraction thereof is administered to a subject, IgE antibody secretion and the degranulation of mast cells and basophils in the subject can be inhibited, and particularly, Th2 immunity can be effectively inhibited so that allergic reactions in vivo can be effectively inhibited. Allergic diseases that may be prevented or treated by the administration may include, without limitation, various diseases caused by various allergens, and include not only pathological symptoms attributable to antigen-antibody reactions, but also those that are very similar to diseases showing antigen-antibody reactions but do not show antigen-antibody reactions, or those that are highly likely to cause such reactions, etc. The allergic diseases include any disease appearing in the allergic respiratory disease or respiratory system, the digestive system, the circulatory system or the like. Preferably, the allergic disease is one or more selected from the group consisting rhinitis, asthma, atopic dermatitis, allergic conjunctivitis, allergic otitis media, allergic gastroenteritis, anaphylaxis and urticaria.

The subject refers to an animal. Specifically, the subject is a mammal in which prevention or treatment with the extract or fraction of the present invention can exhibit a beneficial effect. Preferred examples of the subject include Primates such as humans. In addition, such subjects include all subjects having allergic symptoms or being at risk of developing such symptoms. An amount effective for the prevention or treatment of allergic disease refers to an amount that provides, in single or multiple doses, alone or in combination with one or more other compositions (other therapeutic agents against allergic diseases), a desired outcome in or a benefit to a subject.

In another aspect, the present invention provides an anti-allergic agent comprising an extract of a plant of the *Justicia* genus or a fraction thereof as an active ingredient.

In still another aspect, the present invention provides a food composition for preventing or alleviating allergic disease comprising an extract of a plant of the *Justicia* genus or a fraction thereof as an active ingredient.

When the extract of a plant of the *Justicia* genus or the fraction thereof, which is contained in the food composition, is administered together with a food, it can inhibit IgE antibody secretion and the degranulation of mast cells and basophils, and particularly, can effectively inhibit Th2 immunity. Accordingly, it can exhibit excellent anti-allergic effects, and thus can effectively prevent or improve allergic disease.

The food composition may be a functional food according to the purpose of the present invention. Therefore, the present invention provides a food composition for preventing or improving allergic disease, wherein the food is a functional health food.

The functional food is a food designed to help regulate the body's natural biorhythms. It is a food given added value by physical, biochemical and bioengineering techniques so that it can act to express the functions of a given food for a particular purpose. This functional food is a processed food designed to defend the body, help regulate the body's natural biorhythms, prevent diseases and help a person recover from diseases. It may contain food-acceptable additives, sweeteners or functional materials.

Examples of the food composition according to the present invention include various foods, for example, beverages, gums, teas, vitamin complexes, health supplement foods, etc. The beverages include natural fruit juice, fruit juice beverages, vegetable beverages, etc. The food composition of the present invention may be formulated as tablets, granules, powders, capsules, liquid solutions, pills or the like according to known methods.

In addition, the food composition of the present invention may further comprise various conventional flavorings, natural carbohydrates, etc. Examples of the flavorings include natural flavorings such as thaumatin or stevia extracts, and synthetic flavorings such as saccharin, aspartame, etc. Examples of the natural carbohydrates include monosaccharides such as glucose or fructose, disaccharides such as maltose or sucrose, polysaccharides such as dextrin or cyclodextrin, sugar alcohols such as xylitol, sorbitol or erythritol, and the like. In addition the food composition of the present invention may further comprise food-acceptable additives, including various nutrients, vitamins, minerals (electrolytes), colorants, pectic acid and its salt, alginic acid and its salt, organic acids such as anhydrous citric acid, protective colloidal thickeners, pH adjusting agents, stabilizers, preservatives, glycerin, alcohol, carbonizing agents as used in carbonated beverages, fruit flesh for preparation of natural fruit juice, fruit juice beverages or vegetable juices, etc. Such additives may be used alone or in combination.

In still another aspect, the present invention provides a cosmetic composition for preventing or improving allergic disease comprising an extract of a plant of the *Justicia* genus or a fraction thereof as an active ingredient.

In the present invention, the cosmetic composition may be formulated as a formulation selected from the group consisting of skin softener, astringent lotion, milk lotion, nourishing cream, massage cream, essence, eye cream, eye essence, cleansing cream, cleansing foam, cleansing water, pack, body lotion, body cream, body oil, body essence, makeup base, foundation, hair dyes, shampoo, rinses and body cleaners.

The cosmetic composition of the present invention may be prepared as various formations using the extract of a plant of the *Justicia* genus or the fraction thereof according to conventional cosmetic preparation methods, and may comprise conventional additives, such as stabilizers, solubilizers, vitamins, pigments and fragrances, which are generally used in the field of cosmetic compositions.

If the cosmetic composition of the present invention is prepared in the form of cosmetic product, shampoo, hair lotion, hair cream, hair gel or the like comprising the extract of a plant of the *Justicia* genus or the fraction thereof, it may be used after dilution with a cleansing solution, astringent solution or wetting solution.

The cosmetic composition of the present invention is preferably prepared in the form of skin softener, lotion, cream or essence.

In the cosmetic composition of the present invention, the extract of a plant of the *Justicia* genus or the fraction thereof may be added to the cosmetic composition in an amount of 0.1 to 10 wt % based on the total liquid weight. In addition, the extract or the fraction of a plant of the *Justicia* genus may be added to the cosmetic composition in an amount of 0.001 to 5 wt %, preferably 0.01 to 3 wt %, based on the total dry weight.

In still another aspect, the present invention provides the use of an extract of a plant of the *Justicia* genus or a fraction thereof for the prevention or treatment of allergic disease.

In still another aspect, the present invention provides the use of an extract of a plant of the *Justicia* genus or a fraction thereof for manufacture of a medicament for preventing or treating allergic disease.

Herein, the extract of a plant of the *Justicia* genus or the fraction thereof, and the allergic disease, are as described above.

It should be understood that the values described in the specification include equivalents thereof unless otherwise specified.

[Mode for Invention]

Hereinafter, preferred Preparation Examples, Examples and Formulation Examples will be described for a better understanding of the present invention. It is to be understood, however, that these Preparation Examples, Examples and Formulation Examples are for illustrative purposes only and are not intended to limit the scope of the present invention.

Preparation Example 1: Preparation of *Justicia procumbens* L. Extract

*Justicia procumbens* L. used in the experiment was collected in a region of South Korea and dried in the shade. The origin of the plant was identified by the National Institute of Biological Resources of the Ministry of Environment (Korea) (identification sample number: NIBRVP0000469673). Using water and organic solvents (ethanol, isopropanol, methanol, n-butanol, n-hexane, ethyl acetate, dichloromethane, ether, chloroform, and acetone) as extraction solvents, *Justicia procumbens* L. extracts were prepared.

Specific methods for preparing the extracts are as follows.

Preparation Example 1.1: Preparation of Water Extracts

*Justicia procumbens* L. dried in the shade was divided into a whole plant, an aerial part, a root, a leaf, a flower and the like, and then pulverized using a pulverizer (KSP-35, Korea Medi Co., Ltd.). Accurately 5 g of each part of the crushed *Justicia procumbens* L. was extracted under reflux with 50 ml of purified water in a constant-temperature incubator (B-09, Hyundai Science Co., Ltd) at 90° C. twice (first extraction: 2 hours, and second extraction: 1 hour). Each of the extracts was naturally filtered through filter paper, and each of the filtrates was concentrated with a vacuum evaporator (N-1100, EYELA) at a temperature of 50-60° C., and then dried in a vacuum oven (OV-12, JEIO Tech) at 60° C. for 12 hours, thereby obtaining 1.05 g. The obtained extracts are shown in Table 1 below.

TABLE 1

| Herbal material weight (part) | Extraction solvent | Amount obtained (g) | Yield (%) |
|---|---|---|---|
| 5 g (whole plant) | Purified water | 1.09 | 21.8 |
| 5 g (aerial part) | Purified water | 1.05 | 20.9 |
| 5 g (root) | Purified water | 0.54 | 10.7 |
| 5 g (leaf) | Purified water | 1.05 | 21.0 |
| 5 g (flower) | Purified water | 0.88 | 17.6 |

Preparation Example 1.2: Preparation of Ethanol Extracts

Using ethanol as an extraction solvent, ethanol extracts of *Justicia procumbens* L. were prepared in the same manner as described in Preparation Example 1.1. Each of the whole plant, aerial part, root, leaf and flower of *Justicia procumbens* L. was extracted to prepare an ethanol extract of each part. In addition, the aerial part of *Justicia procumbens* L. was extracted with 10%, 20%, 30%, 40%, 50%, 60%, 70%, 80%, 90%, 95% or 100% (v/v %) ethanol to prepare ethanol extracts. The extracts were obtained in an amount of 0.16 to 1.04 g as shown in Table 2 below.

TABLE 2

| Herbal material weight (part) | Extraction solvent | Amount obtained (g) | Yield (%) |
|---|---|---|---|
| 5 g (whole plant) | 100% ethanol | 0.21 | 4.17 |
| 5 g (aerial part) | 100% ethanol | 0.20 | 4.07 |
| 5 g (root) | 100% ethanol | 0.16 | 3.23 |
| 5 g (leaf) | 100% ethanol | 0.46 | 9.16 |
| 5 g (flower) | 100% ethanol | 0.27 | 5.49 |

| Herbal material weight (aerial part) | Extraction solvent (concentration) | Amount obtained (g) | Yield (%) |
|---|---|---|---|
| 5 g | 10% ethanol | 0.98 | 19.55 |
| 5 g | 20% ethanol | 1.04 | 20.85 |
| 5 g | 30% ethanol | 0.96 | 19.2 |
| 5 g | 40% ethanol | 0.96 | 19.2 |
| 5 g | 50% ethanol | 0.90 | 17.9 |
| 5 g | 60% ethanol | 0.87 | 17.4 |
| 5 g | 70% ethanol | 0.76 | 15.2 |
| 5 g | 80% ethanol | 0.65 | 12.9 |
| 5 g | 90% ethanol | 0.46 | 9.1 |
| 5 g | 95% ethanol | 0.56 | 11.2 |
| 5 g | 100% ethanol | 0.27 | 5.45 |

Preparation Example 1.3: Preparation of Isopropanol Extracts

Using isopropanol as an extraction solvent, isopropanol extracts of *Justicia procumbens* L. were prepared in the same manner as described in Preparation Example 1.1. Specifically, 5 g of *Justicia procumbens* L. was extracted with 10%, 20%, 30%, 40%, 50%, 60%, 70%, 80%, 90% or 100% (v/v %) isopropanol to prepare isopropanol extracts. The extracts were obtained in an amount of 0.19-1.01 g as shown in Table 3 below.

TABLE 3

| Herbal material weight (part) | Extraction solvent | Amount obtained (g) | Yield (%) |
|---|---|---|---|
| 5 g | 10% isopropanol | 0.96 | 19.25 |
| 5 g | 20% isopropanol | 1.01 | 20.2 |
| 5 g | 30% isopropanol | 1.00 | 19.9 |
| 5 g | 40% isopropanol | 0.96 | 19.15 |
| 5 g | 50% isopropanol | 0.99 | 19.75 |
| 5 g | 60% isopropanol | 0.76 | 15.25 |
| 5 g | 70% isopropanol | 0.59 | 11.7 |
| 5 g | 80% isopropanol | 0.535 | 10.5 |
| 5 g | 90% isopropanol | 0.39 | 7.75 |
| 5 g | 100% isopropanol | 0.19 | 3.85 |

Preparation Example 1.4: Preparation of Extractions Using Other Organic Solvents Using various organic solvents, including methanol, n-butanol, n-hexane, ethyl acetate, dichloromethane, ether, chloroform and acetone, extracts of *Justicia procumbens* L. were prepared. In this Example, unless otherwise specified, the extraction solvent was used with pure (100% v/v) solvent. The extraction was performed in the same manner as described in Preparation Example 1.1, except that a different kind of extraction solvent was used. For preparation of a methanol extract, 3 L of methanol was used for 300 g of pulverized *Justicia procumbens* L. The extracts were obtained in an amount of 0.19 to 1.01 g as shown in Table 4 below.

TABLE 4

| Herbal material weight | Extraction solvent | Amount obtained (g) | Yield (%) |
|---|---|---|---|
| 300 g | Methanol | 15.41 | 5.1 |
| 5 g | n-butanol | 0.22 | 4.3 |
| 5 g | n-hexane | 0.1 | 1.9 |
| 5 g | Ethyl acetate | 0.15 | 2.9 |
| 5 g | Dichloromethane | 0.1 | 2.0 |
| 5 g | Ether | 0.12 | 2.3 |
| 5 g | Chloroform | 0.16 | 3.2 |
| 5 g | Acetone | 0.13 | 2.6 |

Preparation Example 2: Preparation of Organic Solvent Soluble Fractions of 95% Ethanol Extract of *Justicia procumbens* L About 15 g of *Justicia procumbens* L. crushed using a pulverizer was reflux-extracted with 150 ml of 95% ethanol twice (first extraction: 2 hours, and second extraction: 1 hour), in a constant-temperature incubator (B-09, Hyundai Science Co., Ltd) at 90° C. The extract was filtered under reduced pressure, and the filtrate was concentrated in a vacuum evaporator (N-1100, EYELA) at a temperature of 50 to 60° C., and then dried in a vacuum oven (OV-12, JEIO Tech) at 60° C. for 12 hours, thereby preparing a 95% ethanol extract (1.1-1.7 g). The 95% ethanol extract was suspended in 65 ml of distilled water in a separatory funnel, and then 40 ml of each of n-hexane, ethyl acetate and water-saturated n-butanol was added thereto, followed by shaking. After layer separation of the organic solvent in the separatory funnel was confirmed, the organic solvent was concentrated under reduced pressure. The extraction process was repeated three times, thereby preparing an organic solvent fraction (0.1-0.14 g) and a water layer fraction (0.25-0.34 g) excluding the organic solvent layer. The obtained fractions are shown in Table 5 below.

TABLE 5

| Herbal material weight | Fraction | Amount obtained (g) | Yield (%) |
|---|---|---|---|
| 15 g | n-hexane fraction | 0.1 | 0.7 |
|  | Water layer excluding n-hexane | 0.3 | 2.0 |
| 15 g | Ethyl acetate fraction | 0.14 | 0.9 |
|  | Water layer excluding ethyl acetate | 0.34 | 2.3 |
| 15 g | Water-saturated n-butanol fraction | 0.12 | 0.8 |
|  | Water layer excluding water-saturated n-butanol | 0.25 | 1.7 |

Example 1: The Ability of *Justicia procumbens* L. Extract to Inhibit IgE Antibody Secretion In order to confirm the effect of the *Justicia procumbens* L. extract on the inhibition of allergic reactions, the ability of the extract to inhibit IgE antibody secretion was measured using U266B1 cells. The U266B1 cells used were purchased from the American Tissue Cell Culture (ATCC # TIB-196). Specifically, U266B1 cells were diluted in RPMI medium containing 15% fetal bovine serum (FBS) and antibiotics (100 U/mL of penicillin and 100 μg/mL of streptomycin) at a concentration of 2×10$^5$ cells/mL, and then the dilution was dispensed in a 24-well plate at a concentration of 400 μl/well and in a 96-well plate at a concentration of 100 μl/well, and incubated in a 5% $CO_2$ incubator at 37° C. for 72 hours.

The U266B1 cells were treated with 5 mg/mL of each of the *Justicia procumbens* L. extracts and fractions (prepared in Preparation Examples 1 and 2 and shown in Tables 1 to 5). The medium in the 24-well plate was used to measure IgE antibody secretion, and the 96-well plate was used to measure cytotoxicity.

For measurement of IgE antibody secretion, the medium in the 24-well plate was collected and centrifuged at 125×g for 5 minutes to remove debris. 100 g of the medium was diluted 10-fold, and then the degree of IgE secretion was measured using IgE enzyme-linked immonosorbent assay (ELISA, Komabiotech Inc). The inhibition of IgE secretion by each extract was calculated using the following equation 1:

Inhibition (%) of IgE secretion=100−(IgE concentration of test group/IgE concentration of control group)×100  Equation 1

The results of the measurement are shown in Tables 6 to 8 below.

TABLE 6

| | |
|---|---|
| Cell line | U266B1 |
| Concentration of test group | 5 μg/mL |
| | IgE secretion inhibition (%) |
| Test group | (n = 4, Mean ± SE) |
| Water extract | 7 ± 7.0 |
| 10% ethanol extract | 17 ± 4.4 |
| 20% ethanol extract | 18 ± 4.9 |
| 30% ethanol extract | 13 ± 8.0 |
| 40% ethanol extract | 17 ± 4.9 |
| 50% ethanol extract | 37 ± 0.4 |
| 60% ethanol extract | 39 ± 1.8 |
| 70% ethanol extract | 41 ± 2.4 |
| 80% ethanol extract | 53 ± 1.5 |
| 90% ethanol extract | 49 ± 2.2 |
| 95% ethanol extract | 42 ± 2.9 |
| 100% ethanol extract | 53 ± 3.0 |
| 10% isopropanol extract | 18 ± 4.0 |
| 20% isopropanol extract | 14 ± 4.7 |
| 30% isopropanol extract | 17 ± 7.4 |
| 40% isopropanol extract | 17 ± 9.8 |
| 50% isopropanol extract | 23 ± 9.2 |
| 60% isopropanol extract | 29 ± 7.3 |
| 70% isopropanol extract | 33 ± 9.6 |
| 80% isopropanol extract | 46 ± 3.2 |
| 90% isopropanol extract | 47 ± 4.5 |
| 100% isopropanol extract | 52 ± 2.5 |
| Dexamethasone (positive control) | 8 ± 15.0 |

TABLE 7

| | |
|---|---|
| Cell line | U266B1 |
| Concentration of test group | 5 μg/mL |
| | IgE secretion inhibition (%) |
| Test group | (n = 3, Mean ± SE) |
| Whole plant - water extract | 4 ± 2.8 |
| aerial part - water extract | −1 ± 4.5 |
| Root - water extract | 5 ± 0.8 |
| Leaf - water extract | 3 ± 1.9 |
| Flower - water extract | 5 ± 3.2 |
| Whole plant - 100% ethanol extract | 36 ± 2.5 |

TABLE 7-continued

| | |
|---|---|
| aerial part - 100% ethanol extract | 35 ± 4.2 |
| Root - 100% ethanol extract | 29 ± 2.6 |
| Leaf - 100% ethanol extract | 28 ± 0.9 |
| Flower - 100% ethanol extract | 26 ± 2.7 |

TABLE 8

| | |
|---|---|
| Cell line | U266B1 |
| Concentration of test group | 5 μg/mL |
| | IgE secretion inhibition (%) |
| Test group | (n = 3, Mean ± SE) |
| 100% ethanol extract | 36 ± 4.1 |
| 100% isopropanol extract | 38 ± 4.8 |
| Methanol extract | 30 ± 5.1 |
| n-butanol extract | 59 ± 2.4 |
| n-hexane extract | 26 ± 10.0 |
| Ethyl acetate extract | 58 ± 2.6 |
| Dichloromethane extract | 51 ± 2.5 |
| Ether extract | 45 ± 3.2 |
| Chloroform extract | 51 ± 2.6 |
| Acetone extract | 58 ± 2.8 |
| n-hexane fraction | 64 ± 1.6 |
| Water layer excluding n-hexane | 24 ± 0.8 |
| Ethyl acetate fraction | 69 ± 2.6 |
| Water layer excluding ethyl acetate | 1 ± 3.4 |
| Water-saturated n-butanol fraction | 71 ± 2.0 |
| Water layer excluding water-saturated n-butanol | 21 ± 6.5 |
| Dexamethasone (positive control) | 4 ± 3.4 |

As can be seen in Tables 6 to 8, the lower-alcohol and organic solvent extracts of *Justicia procumbens* L. showed the effect of significantly inhibiting IgE secretion from B lymphocytes. In addition, as can be seen in Table 7 above, the ethanol extracts of all the parts of *Justicia procumbens* L. showed an IgE secretion inhibition of about 25-40%.

As can be seen in Table 8 above, various organic solvent fractions, shown in Table 5 and obtained by secondarily extracting the 95% ethanol crude extract, also exhibited excellent inhibitory effects against IgE secretion from B lymphocytes. Thus, it can be seen that the organic solvent extracts of *Justicia procumbens* L. and fractions thereof can effectively inhibit allergic reactions by inhibiting IgE secretion.

In addition, a cytotoxicity experiment was performed using a 96-well plate. The cell viability of cells cultured for 72 hours was measured using a CCK-8 assay kit (Dojindo, Japan). As a result, it was shown that all the *Justicia procumbens* L. extracts and fractions shown in Tables 6 to 8 showed a cell viability of 80% or higher. This suggests that the organic solvent extracts of *Justicia procumbens* L. and fractions thereof can be used as safe substances having no cytotoxicity.

Example 2: Measurement of the Ability of *Justicia procumbens* L. Extract to Inhibit Degranulation In order to measure the degranulation inhibitory abilities of the *Justicia procumbens* L. extracts and fractions shown in Tables 1 to 5 above, β-hexosaminidase secretion from mast cells and basophils was measured to determine the degranulation inhibitory abilities (de Haan et al. Lipid-rich enteral nutrition regulates mucosal mast cell activation via the vagal anti-inflammatory reflex. *American Journal of Physiology-Gastrointestinal and Liver Physiology* 305.5 G383-G391, 2013; Sewell et al. Induction of interleukin-4 and interleukin-5 expression in mast cells is inhibited by glucocorticoids. *Clinical and diagnostic laboratory immunology* 5.1 18-23, 1998).

MC/9 mouse mast cells were purchased from the American Tissue Cell Culture (ATCC # CRL-8306), and RBL-2H3 rat basophilic cells were purchased from the Korean Cell Link Bank (KCLB #22256). MC/9 mast cells and RBL-2H3 basophils were diluted at concentrations of $2 \times 10^6$ cells/mL and $5 \times 10^5$ cells/mL, respectively, and 400 µl of each of the dilutions was dispensed into each well of 24-well plates. Each well was pretreated with 10 µg/mL or 20 µg/mL of each of the extracts and fractions (prepared in Preparation Examples 1 and 2 and shown in Tables 1 to 5 above) for 30 minutes, and then degranulation of the cells was induced with 200 nM PMA/10 mM A23187 for 1 hour. A normal group was treated with DMSO, and a control group was treated with PMA/A23187 alone. Each of β-hexosaminidase released into the medium by degranulation and β-hexosaminidase in a cell lysate obtained by lysis with 1% Triton-X100 was incubated with 4-p-Nitrophenyl-N-acetyl-β-D-glucosaminide (Sigma # N-9376) at 37° C. for 1 hour, and then 0.2M glycine (pH 10.7) was added to stop the reaction. The absorbance at 405 nm was measured, and β-hexosaminidase secretion (%) was calculated using the following equation 2:

β-hexosaminidase secretion (%)={absorbance of medium/(absorbance of cell lysate+absorbance of medium)}×100        Equation 2

Based on β-hexosaminidase secretion (%) obtained using equation 2 above, the degranulation inhibitory ability of each of the *Justicia procumbens* L. extracts was calculated using the following equation 3 (β-heXo: β-hexosaminidase):

Degranulation inhibitory ability (%)={(β-hexo secretion % of test group−β-hexo secretion % of normal group)/(β-hexo secretion % of control group−β-hexo secretion % of normal group)}×100        Equation 3

The results of the calculation are shown in Tables 9 to 11 below.

TABLE 9

| | Inhibition (%) of degranulation (n = 3, Mean ± SE) Cell line | |
|---|---|---|
| | MC/9 | RBL-2H3 |
| | concentration | |
| Test group | 20 µg/mL | 20 µg/mL |
| Water extract | 6 ± 3.1 | 4. ± 1.6 |
| 10% ethanol extract | 22 ± 1.1 | 7 ± 2.9 |
| 20% ethanol extract | 21 ± 2.0 | 9 ± 1.3 |
| 30% ethanol extract | 22 ± 0.8 | 16 ± 1.5 |
| 40% ethanol extract | 13 ± 3.6 | 13 ± 5.5 |
| 50% ethanol extract | 44 ± 0.1 | 16 ± 1.3 |
| 60% ethanol extract | 33 ± 0.2 | 12 ± 5.5 |
| 70% ethanol extract | 59 ± 0.7 | 10 ± 0.7 |
| 80% ethanol extract | 43 ± 2.3 | 12 ± 4.0 |
| 90% ethanol extract | 44 ± 2.2 | 13 ± 1.9 |
| 95% ethanol extract | 46 ± 0.9 | 30 ± 1.3 |
| 100% ethanol extract | 61 ± 1.2 | 42 ± 1.6 |
| 10% isopropanol extract | 14 ± 1.7 | 6 ± 3.4 |
| 20% isopropanol extract | 23 ± 1.6 | 11 ± 2.4 |
| 30% isopropanol extract | 16 ± 1.9 | 15 ± 3.6 |
| 40% isopropanol extract | 21 ± 3.6 | 10 ± 1.7 |
| 50% isopropanol extract | 27 ± 1.9 | 18 ± 2.4 |
| 60% isopropanol extract | 37 ± 3.9 | 14 ± 2.3 |
| 70% isopropanol extract | 33 ± 6.5 | 13 ± 3.5 |
| 80% isopropanol extract | 45 ± 2.8 | 12 ± 2.5 |
| 90% isopropanol extract | 42 ± 9.8 | 15 ± 3.3 |
| 100% isopropanol extract | 50 ± 0.6 | 30 ± 2.0 |
| Dexamethasone (positive control) | 64 ± 0.2 | 18 ± 1.0 |

TABLE 10

| | Inhibition (%) of degranulation (n = 3, Mean ± SE) Cell line RBL-2H3 concentration |
|---|---|
| Test group | 10 µg/Ml |
| Whole plant - water extract | 0 ± 3.9 |
| aerial part - water extract | 2 ± 1.9 |
| Root - water extract | 7 ± 3.5 |
| Leaf - water extract | 5 ± 3.4 |
| Flower - water extract | 2 ± 1.8 |
| Whole plant - 100% ethanol extract | 24 ± 1.7 |
| aerial part - 100% ethanol extract | 28 ± 1.3 |
| Root - 100% ethanol extract | 17 ± 5.7 |
| Leaf - 100% ethanol extract | 19 ± 1.1 |
| Flower - 100% ethanol extract | 12 ± 3.0 |

TABLE 11

| | Degranulation inhibition (%) (n = 3, Mean ± SE) Cell line | |
|---|---|---|
| | MC/9 | RBL-2H3 |
| | concentration | |
| Test group | 10 µg/mL | 10 µg/mL |
| 100% ethanol extract | 59 ± 1.1 | 27 ± 2.0 |
| 100% isopropanol extract | 42 ± 1.1 | 19 ± 1.3 |
| Methanol extract | 40 ± 0.6 | 22 ± 0.9 |
| n-butanol extract | 60 ± 1.5 | 33 ± 2.7 |
| n-hexane extract | 73 ± 0.3 | 36 ± 2.6 |
| Ethyl acetate extract | 39 ± 1.1 | 26 ± 1.0 |
| Dichloromethane extract | 52 ± 0.2 | 36 ± 0.5 |
| Ether extract | 59 ± 1.8 | 42 ± 1.0 |
| Chloroform extract | 73 ± 1.4 | 37 ± 1.8 |
| Acetone extract | 43 ± 1.3 | 33 ± 3.6 |
| n-hexane fraction | 57 ± 1.7 | 25 ± 1.0 |
| Water layer excluding n-hexane | 70 ± 1.7 | 20 ± 0.6 |
| Ethyl acetate fraction | 31 ± 1.0 | 25 ± 6.7 |
| Water layer excluding ethyl acetate | 68 ± 1.0 | 18 ± 8.3 |
| Water-saturated n-butanol fraction | 33 ± 0.6 | 22 ± 2.0 |
| Water layer excluding water-saturated n-butanol | 59 ± 1.1 | 10 ± 2.4 |
| Dexamethasone (positive control) | 35 ± 0.2 | 14 ± 3.0 |

As can be seen in Tables 9 to 11 above, the lower alcohol extracts and organic solvent extracts of *Justicia procumbens* L. all inhibited the degranulation of mast cells and basophils.

As can be seen in Table 10 above, the ethanol extract of each part of *Justicia procumbens* L. showed a high inhibition of degranulation of 12-28%. Particularly, the ethanol extracts of the whole plant and aerial part showed a very high ability to inhibit the degranulation of basophils. In addition, as can be seen in Table 11 above, the organic solvent fractions, shown in Table 5 and obtained by secondarily extracting the 95% ethanol crude extract, also showed an excellent ability to inhibit the degranulation of mast cells and basophils.

From the above-described results, it can be seen that the organic solvent extracts of *Justicia procumbens* L. and their fractions can effectively allergic reactions by inhibiting the degranulation of mast cells and basophils.

Example 3: Examination of Inhibition of IgE Secretion in Balb/c Mouse Rhinitis Models In order to confirm whether the *Justicia procumbens* L. extract of the present invention can actually inhibit allergic reactions in animal models, inhibition of IgE secretion in Balb/c mouse rhinitis models was examined.

Specifically, 5-week-old Balb/c mice were purchased and acclimated for 1 week. On 0, 7 and 14 days of one week of acclimation, the mice were systematically sensitized by intraperitoneally injecting 0.1% ovalbumin (OVA: 1 mg/mL, Al(OH)$_3$: 20 mg/ml) in an amount of 100 μl/mouse. From one week after the final systemic sensitization, 200 mg/kg of the 95% ethanol extract prepared in Preparation Example 1 was orally administered to the mice in the morning every day for 1 week. As a positive control, 3 mg/kg of dexamethasone was intraperitoneally administered. After 1 hour, 0.4% ovalbumin solution was dropped into the nasal cavity. In the afternoon, 0.4% ovalbumin solution was dropped once more into the nasal cavity. After 7 days of drug administration, the mice were biopsied, and whole blood was sampled from the inferior vena cava and centrifuged at 12000 rpm for 10 minutes to separate serum. The IgE concentration in the separated serum was measured using enzyme-linked immonosorbent assay (ELISA, Komabiotech Inc), and the results of the measurement are shown in Table 12 below. The inhibition (%) of IgE secretion was calculated using the following equation 4:

Inhibition (%) of secretion=100−{(concentration in test group−concentration in normal group)/(concentration in ovalbumin-induced group−concentration in normal group)}×100     Equation 4

TABLE 12

|  | Serum IgE concentration (ng/mL, Mean ± SE) | Inhibition of IgE secretion (%, Mean ± SE) |
|---|---|---|
| Normal group | 9.3 ± 3.7 | — |
| Ovalbumin-induced group | 79.4 ± 6.4 | — |
| Group treated with *Justicia procumbens* L. extract | 35.7 ± 8.8 | 62.4 ± 12.5 |
| Dexamethasone (positive control) | 32.2 ± 4.4 | 67.3 ± 6.3 |

As can be seen in Table 12 above, the *Justicia procumbens* L. extract inhibited IgE secretion in the allergic rhinitis models by about 60% or more, and thus exhibited an effect similar to that of dexamethasone used as the positive control. Thus, it was found that the *Justicia procumbens* L. extract can be used as a potential therapeutic agent for allergic rhinitis instead of dexamethasone. Particularly, dexamethasone is prescribed only for severe allergic rhinitis, whereas it is expected that the *Justicia procumbens* L. can also be prescribed for mild allergic rhinitis, because it is an herbal extract.

Example 4: Examination of the Ability to Inhibit Anaphylaxis

In order to confirm the effect of the *Justicia procumbens* L. extract on the inhibition of allergic reactions, the effect of the *Justicia procumbens* L. extract on the inhibition of shock death in ICR mouse anaphylaxis models was examined.

Specifically, ICR mice were grouped (n=10/group) according to body weight. The mice were fasted from one day before the experiment, and then Compound 48/80 (Sigma # C2313) was administered intraperitoneally to the mice at a concentration of 16 mg/kg to induce anaphylaxis. At one hour before induction of anaphylaxis, each of 100 mg/kg of the 95% ethanol extract of *Justicia procumbens* L., prepared in Preparation Example 1, and 200 mg/kg of the positive control DSCG (Cromolyn sodium, Sigma # C0399), was administered intraperitoneally to the mice. The mortality of the mice was observed for 20 minutes after induction of anaphylaxis, and the results of the observation are shown in Table 13 below. The inhibition (%) of anaphylaxis was calculated using the following equation 5:

Inhibition (%) of anaphylaxis=100−(number of dead mice/total number (10 mice) of mice)×100     Equation 5

TABLE 13

|  | Inhibition (%) of anaphylaxis |
|---|---|
| Compound 48/80 | — |
| Group treated with *Justicia procumbens* L. extract | 90 |
| DSCG (positive control) | 60 |

As can be seen in Table 13 above, the *Justicia procumbens* L. extract inhibited anaphylaxis by about 90%, indicating that it has a very excellent ability to inhibit anaphylaxis. This inhibitory effect of the *Justicia procumbens* L. extract was very significant compared to the inhibitory effect of the positive control DSCG (an inhibition of about 60%). Thus, it was found that the *Justicia procumbens* L. extract can effectively inhibit anaphylactic shock death due to its excellent effect on the inhibition of allergic reactions.

Example 5: Effect on Inhibition of Asthma in Balb/c Mouse Asthma Models

Using the water extract, 95% ethanol extract and 100% ethanol extract of *Justicia procumbens* L. prepared in Preparation Example 1, changes in various markers associated with asthma disease in Balb/c mouse asthma models were measured.

5-week-old Balb/c mice were purchased and acclimated for 1 week. On 0 and 14 days of 1 week of acclimation, the mice were systematically sensitized by intraperitoneally administering 0.1% ovalbumin (OVA: 1 mg/mL, Al(OH)$_3$: 20 mg/mL) in an amount of 100 μl/mouse. From one week after the final systematic sensitization (21 days), 200 mg/kg of each of the water extract, 95% ethanol extract and 100% ethanol extract of *Justicia procumbens* L. prepared in Preparation Example 1 was administered orally to the mice every day for 10 days. As a positive control, 3 mg/kg of dexamethasone was administered intraperitoneally. After one hour, 0.2% ovalbumin solution was sprayed and inhaled into the mice for 1 hour by use of a nebulizer (PARI Boy SX, Germany GmbH). 5 hours after final sensitization (30 days), the mice were biopsied, and whole blood was sampled from the mice and centrifuged at 12000 rpm for 10 minutes to separate serum. In addition, the lung tissue was isolated from each mouse and flushed with 1 mL of phosphate buffered saline through tracheostomy to collect bronchoalveolar lavage fluid (BALF). The collected bronchoalveolar lavage fluid was centrifuged at 3000 rpm for 10 minutes, and the supernatant was used to measure physiologically active substances (IL-4, and IL-5), and the pellets were used to measure the number of inflammatory cells.

The IgE concentration in the separated serum was measured using IgE enzyme-linked immonosorbent assay (ELISA, Komabiotech Inc.), and the physiologically active substances (interleukin-4 (IL-4) and interleukin-5 (IL-5)) in the isolated bronchoalveolar lavage fluid were measured using an enzyme-linked immonosorbent assay (ELISA, IL-4: Enzo # ADI-900-043, IL-5: R&D system # M5000) corresponding to each substance. The results of the measurement are shown in Table 14 below, and the ability of each extract to inhibit IgE secretion was calculated in the same manner as equation 4 shown in Example 3.

In addition, the bronchoalveolar lavage fluid pellets were re-dissolved in 0.5 mL of phosphate buffered saline, and 0.1 mL of the solution was added to each well of a 96-well plate and centrifuged at 800 rpm for 5 minutes to attach the cells to the bottom (3 wells per sample). Then, each sample was stained with Diff Quik staining solution (Sysmex), and photographed with a microscope at 2-6 random sites. About 200 cells per sample were counted to calculate the percentage (%) of inflammatory cells of each group. The total number of inflammatory cells was measured with a microscope using a hematocytometer, and the number of basophils was calculated using the percentage (%) of each inflammatory cells, and is shown in FIG. 1. Statistical processing was performed using an SPSS program, and a Levene test was performed for a test for equal variance, and significance was tested by one-way analysis (ANOVA).

TABLE 14

| Mean ± SD | Serum IgE concentration (ng/mL) (inhibition of IgE secretion, (%)) | Bronchoalveolar lavage fluid IL-4 (pg/mL) (inhibition of IgE secretion, (%)) | Bronchoalveolar lavage fluid IL-5 (pg/mL) (inhibition of IgE secretion, (%)) |
|---|---|---|---|
| Normal group | 21.6 ± 5.0 (—) | 40.9 ± 1.0 (—) | 4.3 ± 1.4 (—) |
| Ovalbumin-induced group | 107.2 ± 5.0* (—) | 96.2 ± 1.0* (—) | 38.7 ± 6.6* (—) |
| Group treated with water extract of *Justicia procumbens* L. | 83.2 ± 11.1 (28.0 ± 13.0) | 73.5 ± 2.9 # (40.9 ± 5.2) | 35.3 ± 5.9 (9.9 ± 17.1) |
| Group treated with 95% ethanol extract of *Justicia procumbens* L. | 67.7 ± 2.6 # (46.2 ± 3.0) | 83.3 ± 4.0 # (23.4 ± 7.2) | 28.0 ± 3.3 # (31.2 ± 9.5) |
| Group treated with 100% ethanol extract of *Justicia procumbens* L. | 34.1 ± 9.6 # (85.4 ± 11.2) | 58.5 ± 2.5 # (68.1 ± 4.6) | 18.7 ± 4.2 # (58.0 ± 12.1) |
| Dexamethasone (positive control) | 85.8 ± 4.9 # (25.0 ± 5.8) | 56.0 ± 2.1 # (72.7 ± 3.8) | 4.8 ± 3.2 # (98.7 ± 9.2) |

*p < 0.05 vs. normal group,
# p < 0.05 vs. induced group

As can be seen in Table 14 above and FIG. 1, the 95% ethanol extract and 100% ethanol extract of *Justicia procumbens* L. significantly inhibited serum IgE that is an asthma-related marker, and showed a better ability to inhibit IgE secretion, compared to the positive control dexamethasone. In addition, the 95% ethanol extract and 100% ethanol extract of *Justicia procumbens* L. also reduced the IL-4 concentration to an extent similar to that shown by the positive control dexamethasone, and significantly reduced the number of inflammatory cells in the bronchoalveolar lavage fluid. Particularly, the 100% ethanol extract showed a very excellent effect of reducing the number of basophils and the total number of inflammatory cells to those of the normal group. From such results, it was found that the *Justicia procumbens* L. extract has an excellent effect on the inhibition of allergic reactions, and thus can effectively treat allergic diseases.

Formulation Example 1: Preparation of Medicaments 1.1: Preparation of Powder

| | |
|---|---|
| Extract of a plant of the genus *Justicia* or a fraction thereof | 100 mg |
| Lactose | 100 mg |
| Talc | 10 mg |

The above components are mixed with one another and filled in an airtight container to prepare powder.

1.2: Preparation of Tablet

| | |
|---|---|
| Extract of a plant of the genus *Justicia* or a fraction thereof | 100 mg |
| Corn starch | 100 mg |
| Lactose | 100 mg |
| Magnesium stearate | 2 mg |

The above components are mixed with one another, and compressed according to a conventional tablet preparation method to prepare a tablet.

1.3: Preparation of Capsule

| | |
|---|---|
| Extract of a plant of the genus *Justicia* or a fraction thereof | 100 mg |
| Corn starch | 100 mg |
| Lactose | 100 mg |
| Magnesium stearate | 2 mg |

According to a conventional capsule preparation method, the above components are mixed with one another and filled in a gelatin capsule to prepare a capsule.

1.4: Preparation of Injectable Solution

| | |
|---|---|
| Extract of a plant of the genus *Justicia* or a fraction thereof | 100 mg |
| Injectable sterile distilled water | q.s. |
| pH adjusting agent | q.s. |

According to a conventional method for preparation of an injectable solution, the above components are used per ampoule (2 ml) to prepare an injectable solution.

1.5: Preparation of Liquid Formulation

| | |
|---|---|
| Extract of a plant of the genus *Justicia* or a fraction thereof | 100 mg |
| Sugar | 20 g |
| Isomerized sugar | 20 g |
| Lemon fragrance | q.s. |

Purified water is added to a total volume of 1,000 ml. According to a conventional method for preparation of a liquid formulation, the above components are mixed with one another, and then filled in a brown bottle and sterilized to prepare a liquid formulation.

Formulation Example 2: Preparation of Food

| Extract of a plant of the genus Justicia or a fraction thereof | 100 mg |
|---|---|
| Vitamin mixture | q.s. |
| Vitamin A acetate | 70 μg |
| Vitamin E | 1.0 mg |
| Vitamin B1 | 0.13 mg |
| Vitamin B2 | 0.15 mg |
| Vitamin B6 | 0.5 mg |
| Vitamin B12 | 0.2 μg |
| Vitamin C | 10 mg |
| Biotin | 10 μg |
| Amide nicotinate | 1.7 mg |
| Folic acid | 50 μg |
| Calcium pantothenate | 0.5 mg |
| Mineral mixture | q.s. |
| Ferrous sulfate | 1.75 mg |
| Zinc oxide | 0.82 mg |
| Potassium phosphate monobasic | 15 mg |
| Potassium phosphate dibasic | 55 mg |
| Potassium citrate | 90 mg |
| Calcium carbonate | 100 mg |
| Magnesium chloride | 24.8 mg |

Although the contents of the vitamins and the mineral mixture are preferably those suitable for health functional foods, these contents may be optionally modified. According to a conventional method for preparation of health functional food, the above components are mixed with one another, and then prepared into a health functional food (e.g., nutritional candy) according to a conventional method.

Formulation Example 3: Preparation of Beverage

| Extract of a plant of the genus Justicia or a fraction thereof | 100 mg |
|---|---|
| Citric acid | 1000 mg |
| Oligosaccharide | 100 g |
| Plum concentrate | 2 g |
| Taurine | 1 g |

Purified water is added to a total volume of 900 ml. According to a conventional method for preparation of a health functional beverage, the above components are mixed with one another, and then stirred with heating at 85° C. for about 1 hour. Then, the resulting solution is filtered, and collected in a 2-liter sterilized container. Next, it is sealed, sterilized, cold-stored, and then used in the preparation of the health functional beverage composition of the present invention.

Although the above composition is a preferable example of components relatively suitable for favorite beverages, the contents thereof may be optionally modified according to regional and national preferences, including consumer characteristics, consumer nations, the intended use, etc.

Formulation Example 4: Preparation of Cosmetic Composition

| Extract of a plant of the genus Justicia or a fraction thereof | 100 mg |
|---|---|
| Glycerin | 3.0 mg |
| Hydrogenated lecithin | 1.0 mg |
| Cetostearyl alcohol | 2.0 |
| Polysorbate 60 | 1.5 |
| Antioxidant | 0.3 |
| Preservative | q.s. |
| Purified water | q.s. |

INDUSTRIAL APPLICABILITY

As described above, the composition comprising an extract of a plant of the Justicia genus or a fraction thereof according to the present invention may be used to prevent, treat or improve allergic disease.

The invention claimed is:

1. A method for treating allergic disease, the method comprising a step of administering to a subject a composition comprising an extract of a plant of the Justicia genus or a fraction thereof,
wherein the plant of the Justicia genus is Justicia procumbens L., and the extract is an organic solvent extract.

2. The method of claim 1, wherein the Justicia procumbens L. is one or more selected from the group consisting of a whole plant, aerial part, root, leaf and flower of the Justicia procumbens L.

3. The method of claim 1, wherein the organic solvent is one or more selected from the group consisting of a lower alcohol having 1 to 4 carbon atoms, hexane, ethyl acetate, dichloromethane, ether, chloroform, and acetone.

4. The method of claim 3, wherein the lower alcohol having 1 to 4 carbon atoms is one or more selected from the group consisting of methanol, ethanol, propanol, isopropanol, butanol and n-butanol.

5. The method of claim 1, wherein the fraction is an organic solvent fraction obtained by fractionation with an organic solvent selected from the group consisting of n-hexane, ethyl acetate and water-saturated n-butanol.

6. The method of claim 1, wherein the fraction is a water fraction excluding an organic solvent.

7. The method of claim 1, wherein the allergic disease is allergic respiratory disease.

8. The method of claim 1, wherein the allergic disease is one or more selected from the group consisting of rhinitis, asthma, atopic dermatitis, allergic conjunctivitis, allergic otitis media, allergic gastroenteritis, anaphylaxis and urticaria.

* * * * *